United States Patent [19]
De Castro et al.

[11] Patent Number: 5,437,772
[45] Date of Patent: Aug. 1, 1995

[54] PORTABLE LEAD DETECTOR

[75] Inventors: Emory S. De Castro, Williamsville; John D. Genders, Marilla, both of N.Y.

[73] Assignee: The Electrosynthesis Co., Inc., Lancaster, N.Y.

[21] Appl. No.: 144,342

[22] Filed: Nov. 1, 1993

[51] Int. Cl.⁶ ............................................. G01N 27/26
[52] U.S. Cl. ................................. 204/153.1; 204/406; 204/412; 204/416; 204/434; 204/400
[58] Field of Search ............... 204/413, 434, 406, 407, 204/412, 416, 400, 153.13, 153.14, 153.16, 153.19, 153.1; 422/82.03

[56] References Cited

U.S. PATENT DOCUMENTS

| | | | |
|---|---|---|---|
| 3,904,487 | 9/1975 | Lieberman et al. | 204/413 |
| 4,343,688 | 8/1982 | Harwood | 204/430 |
| 4,571,292 | 2/1986 | Lui et al. | 204/412 |
| 5,292,423 | 3/1984 | Wang | 204/413 |
| 5,324,400 | 6/1994 | Eliash et al. | 204/434 |

OTHER PUBLICATIONS

"Determination of Lead in Paint By Energy Dispersive X-Ray Flurorescence Spectromety," Kuntz et al., Journal of Coating Technology, 1982, 54(687), p. 63, No month available.

"Rapid Spectrophotometric Determination of Triethyllead, Diethyllead, and Inorganic Lead Ions, and Application to the Determination of Tetraorganolead Compounds," Henderson et al., Analytical Chemistry, 1961, 33, p. 1173, No month available.

"Spot Test Analysis", Jungreis, John Wiley and Sons, New York, 1985, p. 205.

"Analysis with Ion-Selective Electrodes", John Wiley and Sons, 1991, p. 325, No month available.

"On-line sensors for trace metals", Wang, American Laboratory, Jul., 1983, pp. 14-22.

"A Comparative Study of Copper, Lead, Cadmium and Zinc in Human Sweat and Blood", Stuber et al., The Science of the Total Environment, 74 (1988) 235-247, No month available.

"Lead exposure reduction in children: The need for quality environmental laboratories", Breen et al., American Laboratory, Dec. 1992.

"Potentiometric Water Analysis", Midgley et al., John Wiley & Sons, 1991, pp. 325-331, No month available.

"Ultramicroelectrodes", Fleischmann, et al., Datatech Systems, Inc. Science Publishers, 1987, pp. 100-101, 274-275, No month available.

"Laboratory Techniques in Electroanalytical Chemistry", Kissinger, et al., Marcel Dekker, Inc., 1984, pp. 181, 185, No month available.

"Measurement of Cu and Zn in San Diego Bay by Automated Anodic Stripping Voltammetry", Zirino, et al., Environmental Science & Technology, vol. 12, No. 1, Jan, 1978, pp. 73-79.

"Monitoring of the Isotachophoretic Separation of Two Components with an Array Detector", Thormann, et al., Marcel Dekker, Inc., 1985, pp. 995-1011, No month available.

"Rapid Micromethod for Blood Lead Analysis by Anodic Stripping Voltammetry", Morrell, et al., Clinical Chemistry, vol. 22, No. 2, 1976, pp. 221-223. No month availabe.

"Short-Pulse Rapid-Scan Stripping Voltammetry at a Thin Mercury Film Carbon Fiber Electrode", Sottery, et al., Analytical Chemistry, vol. 59, No. 1, Jan. 1987, pp. 140-144.

"Determination of Lead in Paint by Differential-pulse Anodic-stripping Voltammetry", Lai, et al., Analyst, Dec., 1978, vol. 103, pp. 1244-1248.

"Potentiometric Stripping Analysis and Anodic Stripping Voltammetry With Carbon Fiber Electrodes", (List continued on next page.)

*Primary Examiner*—John Niebling
*Assistant Examiner*—Bruce F. Bell
*Attorney, Agent, or Firm*—Howard M. Cohn

[57] ABSTRACT

Apparatus and methods for quickly and easily detecting trace amounts of metallic or non-metallic, electro-active substances, and in particular trace amounts of metals, such as lead in a portable, hand-held detector system with single potential control.

31 Claims, 6 Drawing Sheets

OTHER PUBLICATIONS

Schulze, et al., Analytica Chimica Acta, 159 (1984) 95–103, No month available.

"Electrochemistry at Carbon Fibers", Cushman et al., Analytica Chimica Acta, 130 (1981) 323–327, No month available.

"Thin-Layer Differential Pulse Voltammetry", DeAngelis, et al., Analytical Chemistry, vol. 49, No. 12, Oct. 1977, pp. 1792–1797.

"Instrumental Configurations for the Determination of Sub-Micromolar Concentrations of Electroactive Species with Carbon, Gold and Platinum Microdisk Electrodes in Static and Flow-Through Cells", Bixler, et al., Analytica Chimica Acta, 187 (1986) 67–77, No month available.

"Cyclic Voltammetry and Anodic Stripping Voltammetry with Mercury Ultramicroelectrodes", Wehmeyer, et al., Analytical Chemistry, vol. 57, No. 9, Aug. 1985.

"Theoretical Treatment of Pulsed Voltammetric Stripping at the Thin Film Mercury Electrode", Osteryoung et al., Analytical Chemistry, vol. 46, No. 3, mar. 1974, pp. 351–355.

"Filar Electrodes: Stead-State Currents and Spectroelectrochemistry at Twin Interdigitated Electrodes", Sanderson et al., Analytical Chemistry, vol. 57, No. 12, Oct. 1985, pp. 2388–2393.

"On-Site Measurement of Lead: A Market Opportunity", De Castro, The Electrosynthesis Compnay, Inc. Market Report: Hand-held Lead Detector, No month or year available.

Wang, Stripping Analysis, VCH Publishers, 1985, No month available.

"Interdigitated Microsensor Electrodes" (IMEs), Abtech brochure, Yardley, Pa., No month or year available.

PORTABLE LEAD DETECTOR

This invention was made with Government support under Contract No. 68D2011, awarded by the United States Environmental Protection Agency. The Government has certain rights in this invention.

FIELD OF THE INVENTION

This invention relates to the field of trace metal analysis. More particularly, the invention relates to a portable, hand-held detector system and method of operating the detector system to quickly and easily detect trace amounts of lead, as well as other metals.

BACKGROUND OF THE INVENTION

Lead is an important commodity in the United States wherein approximately $5 \times 10^5$ metric tons of lead per year are consumed. Lead is used in a number of industrial applications including storage batteries, pigments, ammunition, solders, plumbing, cable covering, bearings and caulking, to name a few. Lead's physical properties, which include a low melting point, a high density, low strength, and chemical stability in air, water, and earth, make lead an element of choice for many industrial applications. Because lead is so widely used, lead poisoning is a worldwide problem.

People are exposed to lead from a variety of sources. These include high lead content in soil due to naturally occurring lead concentration, exposure to industrial waste, or fallout from leaded gasoline exhaust. The high lead content in soil is particularly a health problem when compounded with the inability to wash lead from vegetables or fruits. Studies have further found high levels of lead in foods preserved using lead-soldered cans and bottles. Occupational exposure represents a significant risk for workers. Industries, such as automobile manufacturing, ceramic manufacturing, alcoholic beverage manufacturing, and paint manufacturing, all have documented cases of workers suffering from lead poisoning. Lead dust carried on the person of a worker from an industrial site to their home incurs additional risk to children and other family members. Furthermore, lead is being detected in drinking water in numerous cities. This is due to leaching from soldering the pipes of the water distribution system. For each of the above examples, there is a time delay before the symptoms of lead poisoning are recognized because the poisoning is cumulative.

Lead is poisonous because its presence in a person's body inhibits many enzymatic reactions, such as an adverse affect on heme synthesis. Lead intoxication can cause chromosomal aberrations and mutagenicity although there is no evidence that lead is carcinogenic. The OSHA lead standard requires any worker whose blood lead level exceeds 50 micrograms per deciliter ($\mu g/dL$) to be removed from exposure. However, 30 $\mu g/dL$ to 40 $\mu g/dL$ is also believed to pose a significant risk. The Environmental Protection Agency suggests lead in drinking water to be less than 1.5 $\mu g/dL$. Thus, the analytical challenge is to easily and quickly determine the source of chronic lead exposure.

Occupational or natural exposure to lead induces a risk that may not be altogether avoidable. However, during the 1980's, approximately three million children between the ages of six months and five years were found to have poisonous lead levels in their blood. The signs of lead toxicity include headaches, dizziness, abdominal pain, coma, convulsions, manic behavior, and delirium. Virtually all of these cases of lead poisoning could have been prevented through education, awareness, and adequate testing of the environment. A vital link in preventing cases of childhood lead poisoning is determining the degree of lead in the paint used in the child's home.

Analysts measure lead through spectroscopic, photometric and electrochemical techniques. By far the most widely employed method is graphite furnace, Atomic Absorption Spectroscopy (AAS). A sample is digested in acid and placed in a graphite furnace. The characteristic spectral absorption line is monitored and using Beer's Law, related to lead concentration. AAS instruments are expensive and too large for field use. Another measuring technique, X-Ray Fluorescence (XRF) analysis, consists of subjecting a sample to x-rays. The x-rays excite and expel electrons from a given atomic level. By measuring the resulting fluorescence line, the lead concentration can be determined. XRF analysis is extremely sensitive so that this technique suffers from matrix effects. The operator must closely match the sample and reference matrix to achieve accurate results. Even with a highly trained operator, obtaining accurate results is difficult when sampling unknown paint residues.

Researchers have developed some strategies to minimize the matrix problem for XRF analysis as discussed in an article by Kuntz et al. in the Journal of Coating Technology, 1982, 54(687), p. 63. For example, a few laboratories use the photometric method. The photometric method, as discussed in an article by Henderson et al. in the journal Analytical Chemistry, 1961, 33, p. 1173, consists of reacting uncomplexed lead with dithizone, extracting into chloroform, and measuring the absorption maxima at 520 nanometers (nm). This method is deficient because of interferences with other metal ions. Therefore, some experimenters add potassium cyanide (KCN) or other agents (EDTA) to mask the other metals, as discussed in the book by Jungreis entitled *Spot Test Analysis*, John Wiley and Sons, N.Y. 1985, p. 205. The requirement for sample work-up and the interferences make photometric analysis unsuitable for field studies.

A seldom used electrochemical technique is the lead Ion Selective Electrode (ISE) method as discussed by Vesely et al. in a book entitled *Analysis with Ion-Selective Electrodes*, John Wiley and Sons, 1991, p. 325. The lead ISE is like a pH electrode, except a surface specific for lead is used. Poor reproducibility and selectivity over other solution species, like protons and dissolved oxygen, interfere with the results from the lead ISE method.

Another technique used by some laboratories is the Anodic Stripping Voltammetry (ASV) technique for elemental analysis, such as lead in blood and other bodily fluids, see the articles by Morrell et al. in Clinical Chemistry, 1976, 22, p. 221 and Stauber et al. in Science of the Total Environment, 1988, 74, p. 235. A monograph that reviews ASV with respect to applications for determining toxic metal ions, inorganic compounds, and both ionic and neutral organic compounds has been written by Wang, in *Stripping Analysis*, VCH Publishers, 1985. He also details the use of the analogous Cathodic Stripping Voltammetry that is used for a range of similar electro-active substances. The ASV technique typically employs a mercury electrode with a potential impressed thereon causing diluted lead within a solution to be first reduced to metallic lead and then dissolved into the mercury electrode. The partition of lead from solution to the mercury electrode effectively concentrates the lead. Next, an operator using a potentiostat "scans" the potential of the mercury electrode, i.e., constantly adjusts the potential to a series of different, spaced positive potentials, causing oxidation of the dissolved lead back to free ions and its stripping from the mercury electrode. Each metallic element strips from the mercury electrode at a unique potential. Thus, the identity of the metal is determined from the potential at which the element strips out of the mercury. However, the scanning step alone results in a background current, caused by the potential applied to the mercury electrode and the electrical resistance of the analyte solution. The scanning step is also responsible for the faradaic current that corresponds to the presence of lead or other trace elements being oxidized and stripped off from the mercury electrode. Since a simple potential scan can result in a very large background current which ultimately swamps the faradaic signal, researchers often make use of a differential pulse waveform. Here, a voltage pulse is applied to the simple scan. A sophisticated electronic circuit samples the current at discrete times along the pulse, and performs a differential operation of the current. The differential can reduce much of the background current while more clearly resolving the faradaic current. The differential pulse scanning step requires sophisticated electronic circuitry that is both expensive and is packaged in a relatively large case. This technique is commonly called Differential Pulse Anodic Stripping Voltammetry.

The electrochemical steps of the ASV technique generate an analytical signal that enable an operator to test specifically for the presence of lead by selecting the potentials of reduction and oxidation, and a method to preconcentrate dilute lead solutions. Although researchers have reported using the ASV technique for lead in paint, see Lai et al. in Analyst, 1978, 103, p. 1244, the ASV technique for lead analysis has not gained widespread acceptance. As documented by Morrell et al. in Clinical Chemistry, 1976, 22, p. 221, the ASV technique can be as accurate, precise, and as fast as the AAS method for lead analysis. Still, most laboratories use the AAS method, partly due to the difficulties in using the ASV technique for multi-element analysis when both method development and a knowledgeable operator are needed.

A relatively new research area in electroanalytical chemistry is the use and exploitation of microelectrodes to replace traditional, i.e., analytical, electrodes with dimensions in the range from 1.0 $cm^2$ to 0.02 $cm^2$. Neurobiologists began to use electroanalytical techniques to investigate brain chemistry and developed the need for ever-smaller electrodes for in-situ work. By the early nineteen eighties, experimenters in other scientific fields discovered novel properties of electrodes whose diameter ranged from 100's of microns to submicron dimensions, see the article by Fleischmann et al., editors of *Ultramicroelectrodes*, Datatech Systems, Inc. 1987. For example, the low surface area charging of the small electrodes improved the signal to noise ratio during measurements. The need for a small charging current also meant faster kinetic measurements were accessible and measurements could be performed in solutions without supporting electrolytes.

There are various physical forms for microelectrodes. Researchers found that microelectrode properties could not only be achieved with disks of carbon or metal fibers embedded in glass pipettes, but cylinders, drops, rings, bands, lines, and arrays of lines could all be constructed with small enough dimensions to maintain microelectrode behavior. The configuration referred to as arrays of lines is a series of lines formed using, for example, photolithography or silk-screened patterns. One disadvantage of the listed microelectrode configurations, except for the arrays of lines, is that the currents developed during the measurement are on the order of nanoamps, which require special instrumentation for detection thereof.

Sanderson et al. describe the benefits of using an array of twin interdigitated electrodes in an article appearing in Analytical Chemistry, 1985, 57, p. 2388. By using one set of electrodes as a "generator" and the other set of electrodes as a "detector", they show enhanced signal-to-noise ratios (compared to a macro electrode) and, because the array is composed of long bands of electrodes of very small width, they show current levels detectable by conventional electrochemical instrumentation. Thorman et al. use an interdigitated array as a detector for isotachophoresus, see the article in Separation Science and Technology, 1984–1985, 19, p. 995. This article discusses the researcher's control of the potential of each individual electrode. Others have started to investigate the possibility of using interdigitated arrays for flow-through analysis, see Bixtler et al. in Anal. Chim. Acta, 1986, 187, p. 67.

Cushman et al., as discussed in Anal. Chim. Acta. 1981, 130, p. 323, were the first to show the feasibility of the ASV technique performed at a microelectrode. Others have continued to develop the methodology of performing the ASV technique at carbon fiber microelectrodes, see Shulze et al. in Anal. Chim. Acta. 1984, 159, p. 95, and Wehmeyer et al. in Anal. Chem. 1985, 57, p. 1989. The advantages of incorporating the ASV technique with microelectrodes are similar to those discussed before and include enhanced signal to noise and shorter analysis times, as disclosed by Sottery et al. in Anal. Chem. 1987, 59, p. 140; and no requirement for a bulk solution of analyte in using the ASV technique, see Heineman et al. Anal. Chem. 1977, 49, p. 1792, wherein a thin-layer electrochemical cell was employed with a conventional electrode, the ASV technique was used to measure lead, cadmium, and zinc in a 60 $\mu L$ sample volume. Others have developed flowing systems for use in clinical labs, see the article by Wang in Am. Lab. 1983, 7, p. 14 and in the field, see the article by Zirion in Environ. Sci. Technol. 1978, 12, p. 73. Some of these systems offer computer aided automation and control of the process for the ASV technique. All of these systems are large, relatively expensive, and difficult to operate.

OBJECTS AND SUMMARY OF THE INVENTION

It is an object of the present invention to provide a method and apparatus for trace metal analysis to obviate the problems and limitations of the prior art systems.

It is a further object of the present invention to provide a method and apparatus for trace metal analysis wherein an interdigitated electrode array is modified by coating the digits with mercury.

Yet another object is to provide an improved method and apparatus for trace metal analysis wherein a small sample of paint digested in a solution and placed in a portable, handheld detector system which enables the amount of trace lead or other metals to be determined with single potential control.

Still another object is the use of a portable device for detecting toxic species including metals, non-metals, and organics in solids such as soils, paints, foods, building materials, or liquids such as drinking water, beverages, industrial plant processes, effluents, or air, such as incinerators, combustion exhausts, welding operations, and industrial applications.

In accordance with the invention, there is provided a method of and apparatus for trace electro-active substance analysis. A solution having a concentration of at least one trace electro-active substance, such as a trace metal from the group consisting of lead, cadmium, silver, arsenic, cobalt, chromium, iron, mercury, manganese, molybdenum, nickel, selenium, thallium, vanadium, copper, zinc, and/or tin is introduced into a chamber containing a transducer forming an interdigitated array. Then, a first "reducing" potential is applied to the transducer for a first period of time whereby ions of at least one trace electro-active substance, typically lead, are reduced as ions in the solution and concentrated on the element on the collector electrode array. Next, a first "oxidizing" potential is applied to the collector electrode array for a second period of time and simultaneously a "detecting" potential is applied to the detector electrode array for the second period of time whereby the trace electro-active elements concentrated on the collector array are stripped as ions from the collector array back into the solution. The current across the detector electrode array is monitored during said second period of time to determine the amount of trace metals within the solution.

Further, in accordance with the invention, electro-active substances can be other ionic as well as non-ionic substances. For the wider group of analytes, a single potential control method analogous to either anodic or cathodic stripping voltammetry, or simple voltammetry is employed depending on whether the electro-active species is reducible or oxidizable. Representative electro-active species of this broader class include halogen species (for example $Cl-$, $Br-$, $I-$, $Cl_2$, $Br_2$, $I_2$, $ClO-$, $BrO-$, $ClO_2-$, $ClO_3-$, $BrO_3-$, $IO_3-$, $ClO_4-$, $BrO_4-$, $IO_4-$, etc.); cyanides, cyanates; nitrites; sulfides, sulfites, thiosulfates; thiocyanates; arsenites, arsenates; phosphites; phenolates; peroxides; as well as other electro-active ionic species containing such elements as halogen, sulfur, nitrogen, arsenic, phosphorus, oxygen, carbon, etc.

According to the invention, electro-active, non-ionic substances could include organic compounds. An example of the classes of compounds relevant for analysis would be: food additives such as antioxidants; agricultural products such as pesticides and fungicides; pharmaceuticals; and toxic or environmentally controlled substances in general. For example, antioxidants include: ascorbic acid, sodium ascorbate, calcium ascorbate, ascorbic palmitate, butylated hydroxyanisole (BHA), butylated hydroxytoluene (BHT), erythorbic acid, thiodipropionic acid, tert-butylhydroquinone (TBHQ); pesticides and fungicides include these classes: nicotinoids, pyrethroids, rotenoids, dinitrophenols, organothiocyanates, organophosphorus esters, carbamates; fumigants include: hydrogen cyanide, methyl bromide, $\beta, \beta''$-dichlorodiethyl ether, naphthalene and p-dichlorobenzene; pharmaceuticals include: penicillins, tetracyclines, 2-thiobarbituric acid and similar compounds, ethylestradiol, methyl testosterone; and toxic or environmentally controlled substances would include: aldehydes (for example acetaldehyde), ketones, hydrazines, organohalogen compounds (for example dibromoethane or methylene chloride), chelating agents, anilines, benzidines, as well as many other compounds listed for example by the Environmental Protection Agency in the Clean Water and Clean Air Acts.

Also in accordance with the invention, the transducer includes a collector electrode array and detector electrode array each constructed of a monolithic, digitated array having a plurality of spaced digits which can be coated with a layer of mercury. The digits are from an inert conductive material selected, for example, from the group consisting of gold, platinum, iridium, indium, tin oxide, indium on tin oxide, Ebonex TM, silver, graphite, glassy carbon, and conductive carbon.

Further in accordance with the invention, for the application of trace metals in a solid matrix, it will be necessary to extract the free metal(s) from sample matrices into a solution to be analyzed. This toxic metal extracting solution can consist of an acid, an organic solvent, and/or a complexing agent. The organic solvent is selected, for example, from the group comprising ketones, esters, hydrocarbons, halogenated hydrocarbons, and ethers. The acid is selected, for example, from the group comprising inorganic or organic acids. The complexing agent is selected, for example, from the group comprising ammonia, amines, nitrilotriacedic acid, ethylene diamine tetraacetic acid, and other metal chelates.

In accordance with the invention, an interdigitated array is constructed of a first electrode array and a second electrode array each constructed of a monolithic, digitated array having a plurality of spaced digits which can be coated with a layer of mercury. The spaced digits are constructed of a material selected from the group of inert conducting materials, for example, gold, platinum, iridium, graphite, and conductive carbon and may or may not be coated with a layer of mercury about 10 nm to about 1000 nm thick.

BRIEF DESCRIPTION OF THE DRAWINGS

The structure, operation, and advantages of the presently preferred embodiment of the invention will become further apparent upon consideration of the following description taken in conjunction with the accompanying drawings, wherein.

DETAILED DESCRIPTION OF THE INVENTION

Figure 1:
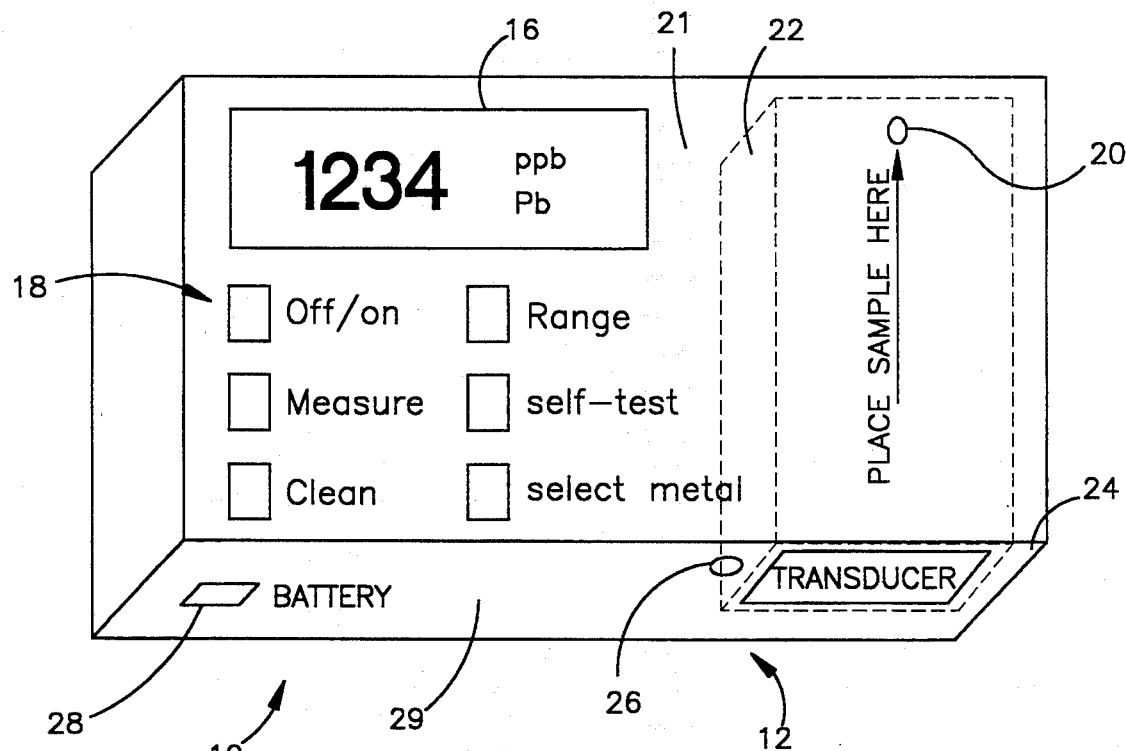
FIG. 1 is a perspective view of a schematic representation of a portable detector device to detect trace amounts of a metal, in accordance with the invention.
Figure 3:
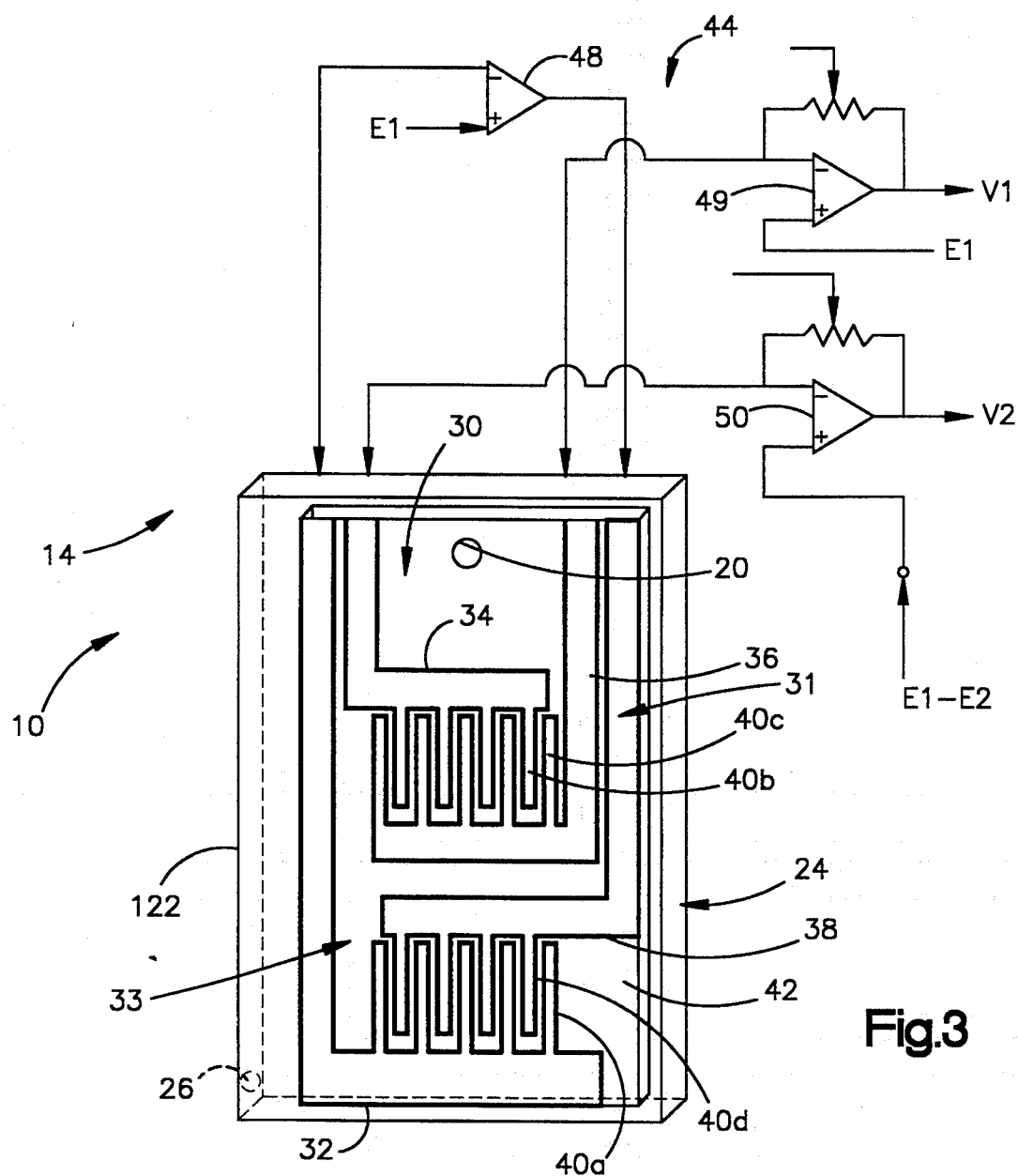
FIG. 3 is a schematic representation of an exemplary circuit for controlling the potential and measuring the current of the collector and detector electrodes of an interdigitated transducer, in accordance with the present invention.
Figure 3A:
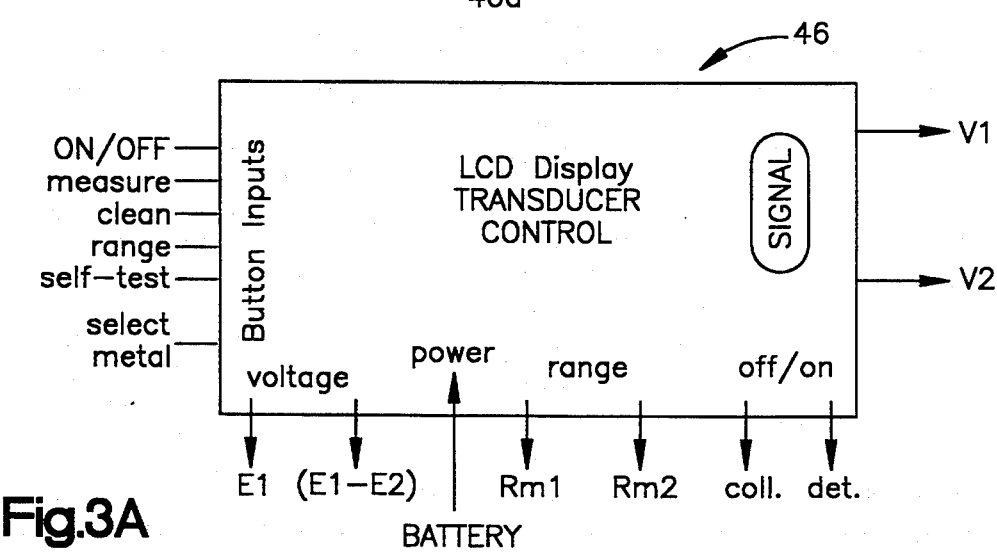
FIG. 3A is a schematic representation of control electronics.

Referring to FIGS. 1 and 3, there is shown a schematic illustration of a system 10 for trace electro-active substance analysis which is packaged in a box-shaped detector 12 that can be small enough to be hand-held and which contains the means 14, including the circuitry and electronic components, for detecting trace amounts of electro-active substances and in particular, a trace metal such as lead, within a solution of known volume.

Detector 12 has a conventional display 16, such as for example an LCD. Control means 18 such as button inputs, are provided to turn detector 12 on and off, to initiate the measurement of the metal being detected, to clean the measuring system, to set the sensitivity range, to self-test and insure proper working of detector 12, and to select the metal and set the sequence of voltage being applied for determining the concentration of the metal being tested. A small opening 20 is provided in a top wall 21 of detector 12 to insert the liquid sample being tested into a chamber 22 containing a transducer component 24. Chamber 22 typically holds a sample volume of about 50 $\mu L$ to about 1000 $\mu L$. A drain hole 26 is provided to empty chamber 22 after completing a test. A battery 28 to power detector 12 can be installed through a side wall of detector 12.

A principle feature of this invention relates to the construction of transducer component 24 which is located in chamber 22. Transducer component 24 is a microsensor device 30, such as a Model IME 1550 Series of an Interdigitated Microsensor Electrode, manufactured by AAI-ABTECH of Yardley, Pa. Microsensor device 30 has a plurality of interdigitated microsensor electrode arrays 32, 34, 36, and 38 (32-38) for the simultaneous interrogation of the electrical properties of a sample solution introduced into chamber 22. Each microsensor electrode array 32-34 has a plurality of digits 40a, 40b, 40c, 40d (40a-40d), respectively, typically fabricated from sputtered gold and configured as a planar monolith on an insulating ceramic substrate 42. Each digit 40a-40d has a width of about 5 $\mu m$ to about 15 $\mu m$ and is spaced from an adjacent digit a distance of about 5 $\mu m$ to about 15 $\mu m$. It is also within the terms of the invention to construct digits 40a-40d of conductive carbon or graphite.

An important aspect of the invention relates to digits 40a-40d being coated with a layer of mercury (Hg) having a film thickness of between 35 and 1500 angstroms. The coating of mercury can be applied using a conventional Potentiostat, such as for example, a Model 433A, manufactured by AMEL of Milano, Italy. By increasing the amount of charge produced by the potentiostat, the thickness of the mercury coating increases, as is known to one skilled in the art. This relationship is shown in Table I, where the thickness of the mercury film is directly related to the amount of accumulated charge in millicoulombs (mC). As discussed in more detail hereinafter, as the thickness of the mercury layer increases, its ability to absorb the ions of lead or other trace metals improves.

TABLE I

| Accumulated Charge, mC | Mercury Film Thickness | | |
|---|---|---|---|
| | Hg, volume, $cm^3$ | Thickness, Angstroms | Thickness, Nanometers |
| 2.17 | $3.2 \times 10^{-7}$ | 45 | 4.5 |
| 1.30 | $1.9 \times 10^{-7}$ | 270 | 27.0 |
| 5.00 | $7.6 \times 10^{-7}$ | 1100 | 110.0 |
| 1.40 | $2.1 \times 10^{-7}$ | 300 | 30.0 |

By introducing samples of a solution, i.e., about 50 $\mu L$ to about 1000 $\mu L$, with a trace metal, such as lead, to chamber 22 containing transducer device 24, the amount of trace metal present can be determined. In order to make this determination, microsensor device 30 is configured with two interdigitated arrays 31 and 33. Interdigitated array includes interdigitated microsensor electrode arrays 34 and 36 which comprise the detector electrode and the collector electrode, respectively, and interdigitated array 32 includes interdigitated microsensor electrode arrays 32 and 38 which comprise the reference (Ag/AgCl) electrode and the auxiliary electrode, respectively. The reference and auxiliary electrodes 32 and 38 insure a constant voltage on the collector electrode array 36 and an accurate measurement of the current from detector elector array 34 as is conventionally known to one skilled in the art. The specific uses and purpose of each of these electrodes are discussed in detail below.

Referring to FIGS. 1 and 3, the circuitry 44 which is connected to transducer device 24 and which enables the measurement of the amount of metal in solution to be accomplished includes a microprocessor chip 46, which in turn is connected to the operational amplifiers OA-1, OA-2, OA-3, (48, 49 and 50, respectively). The microprocessor chip 46 is connected to the input buttons 18 on the case 12. The power from battery 28 is connected to the processor 46 so that voltages $E_1$ and $E_1-E_2$ can be supplied to operational amplifiers 48, 49 and 50. As known to one generally skilled in the art and generally shown and discussed in *LABORATORY TECHNIQUES IN ELECTROANALYTICAL CHEMISTRY* by Kissinger, et al., Published by Marcel Dekker, Inc., in N.Y., 1984, Pgs. 181, 185, an operational amplifier 48 having an applied potential voltage $E_1$ is connected between reference electrode 32 and auxiliary electrode 38. Operational amplifier 49 is connected to the collector electrode 36 and operational amplifier 50 is connected to detector electrode 34. Operational amplifier 49 has a potential of $E_1$ while operational amplifier 50 has a voltage of $E_1-E_2$, as explained in detail below. Both operational amplifiers OA-2 and OA-3 include adjustable resisters $R_{M1}$ and $R_{M2}$ which control the current scale and therefore the sensitivity.

Referring to FIGS. 1 and 3, the relationship between button 18 and microprocessor chip 46 are appreciated. The on/off button turns the system 10 on and off. The measure button initiates the potential sequence to collector and detector electrodes 36, 34 after the introduction of the sample to chamber 22. The clean button initiates a potential to both collector and detector electrodes 36, 34 to clean them from trace metals from a previous test. The range button selects a current-scale for OA-2 and OA-3. Generally, the more dilute a sample, the higher the sensitivity needed. Conversely, the more concentrated a sample, the lower the sensitivity required. The self-test button provides an internal testing for items such as battery life, condition and proper mounting of transducer 24. The select metal button loads a specific voltage sequence, which is stored in the memory of microprocessor 46 in order to test for the presence of different metals.

The microprocessor 46 also has a transducer control section which controls transducer 24. The voltage output provides controls voltage to operational amplifiers OA-2 and OA-3 which in turn provide the potential for the collector and detector electrodes 36, 34. $E_1$ is the potential applied to detector electrode array element 34 while $E_1-E_2$ is the applied potential to collector electrode array element 36. The difference in potential is due to the properties of controlling two electrodes simultaneously. The range section of the transducer control selects the value of resistors $R_{M1}$ and/or $R_{M2}$ for output current-to-voltage converters. The off/on control individually turns the transducer electrodes off and/or on. In the illustrated embodiment, voltage $V_2$, corresponding to the current from the detector electrode array, is monitored. However, it may be desirable to monitor the voltage $V_1$ for the current from the collector electrode array. The operational amplifier OA-3 provides a voltage $V_2$ signal which is sent directly to microprocessor 46. The voltage $V_2$ is directly proportional to the amount of a selected trace metal in the sample. The microprocessor 46 calculates the metal concentration based on the signal $V_2$, and perhaps on a standard as well, and sends a signal to the LCD display section which in turn drives the LCD display 16 and warning lights.

Figure 2:
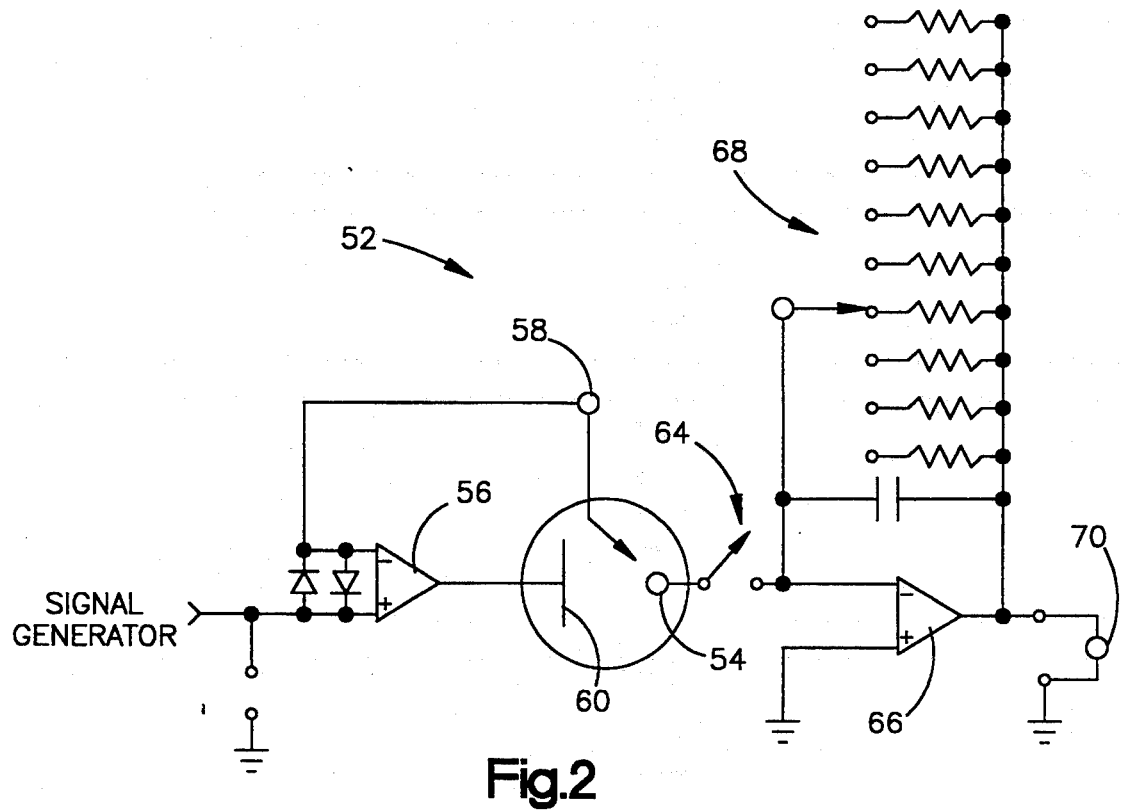
FIG. 2 is a schematic representation of an exemplary circuit for controlling the potential and measuring the current of a single working electrode.

Referring to FIG. 2, there is illustrated a conventional circuit 52 adapted for controlling the potential and measuring the current of a working electrode 54. In general, a potential $E_1$ is applied to the input of an operational amplifier 56 which in turn controls the potential between a reference electrode 58 and a working electrode 54. The operational amplifier 56 is also connected to an auxiliary electrode 60. The output from working electrode 54 is directed through a switch 64 to an operational amplifier 66 which has a sensitivity control 68 provided by a series of parallel resistors R6-R15 which can be individually connected into the circuit. An output from operational amplifier 66 provides a signal which can be read by means such as a meter 70.

To further understand the principles of operation and advantages resulting from the present invention, a general description of the operation of device 12 follows. First, a small sample of a lead containing material, e.g. a chip of paint, is mixed into a predetermined amount of extractant solution, such as an organic solvent system containing an acid such as concentrated nitric acid ($HNO_3$). A small die can be used to cut off the same sized sample for each test. After the paint chip dissolves in the solution, the aqueous phase of the solution is inserted through hole 20 into chamber 22. The collector electrode 36 is initially set at a first reducing potential $E_1$, i.e. at about $-0.4$ Volts (V) to about $-1.2$ V versus Silver/Silver Chloride (Ag/AgCl) for a first time period of about 0.5 to about 20 minutes. This causes the lead ions in the solution to be reduced and deposited in the mercury film coated digits 40c of collector electrode 36. At the same time, any dissolved oxygen is irreversibly reduced. In effect, the lead is removed from the solution and concentrated in the mercury coating digits 40c of collector electrode 36. Next, collector electrode 36 is set at a first oxidizing potential $E_1$, i.e. about 0.10 V to about $-0.5$ V vs. Ag/AgCl for a second time period of about 0.5 to about 20 minutes. During this second time period, the accumulated lead on collector electrode 36 is "stripped" out of the mercury and deposited back into the solution as lead ions. Simultaneously, i.e., during the second time period, detector electrode 34 is set at a first detection potential ($E_1-E_2$), i.e., at about $-0.40$ V to about $-0.70$ V vs. Ag/AgCl causing the lead ions stripped from collector electrode 32 to diffuse between the collector and detector electrodes 36 and 34, respectively. As previously discussed the voltage signal $V_2$, which is picked up from OA-3 and directed to microprocessor 46, is directly proportional to the current generated and hence the lead in the solution. Signal $V_2$ is used by microprocessor 46 to indicate the concentration of lead or other trace elements in the solution. By using fixed potentials, the presence of lead can be selectively analyzed for in a matrix of cadmium, arsenic, silver, cobalt, chromium, iron, mercury, manganese, molybdenum, nickel, selenium, thallium, vanadium, copper, zinc, and/or tin. Unlike Differential Pulse Anodic Stripping Voltammetry, discussed above, the measuring technique of the present invention does not use the voltammetry step which requires scanning and pulsing of the electrode potential. Because the potential is not scanned, the signal noise due to double layer charging when scanning potentials is eliminated and the controlling electronics are vastly simplified. With the system of the present invention, a substantial savings in the device size is achieved because of the use of a transducer incorporating interdigitated electrode arrays, the simplified potential regime, and the thin-layer chamber for housing the transducer.

To prevent the accumulation of lead in the mercury layer about collector electrode 36, a first cleaning potential of about 0.1 V to about $-0.20$ V is applied for a third period of time of about 0.5 to about 20 minutes. Simultaneously, a second cleaning potential of about 0.10 V to about $-0.20$ V is applied to detector electrode 34 to clean the latter of trace metals. These results indicate the need for a cleaning step for single-potential operation, as incorporated in the preferred embodiment of the present invention.

The experiments discussed directly before were conducted with a very thin mercury film on a transducer inserted in a non-flowing cell. Using single potential control and a 27 nanometer (nm) thick film of mercury, a 6 nA signal was obtained for 10 ppm Pb. The same experiment on a 108 nm thick mercury film yielded a 80 nA signal for 10 ppm Pb. The literature (Osteryoung et al., Analytical Chemistry, 1974, 46, p. 351), reports that with typical ASV analysis using a range of mercury films between 10 nm and 1000 nm for the transducers, the thicker film clearly yields better signals.

Figure 4:
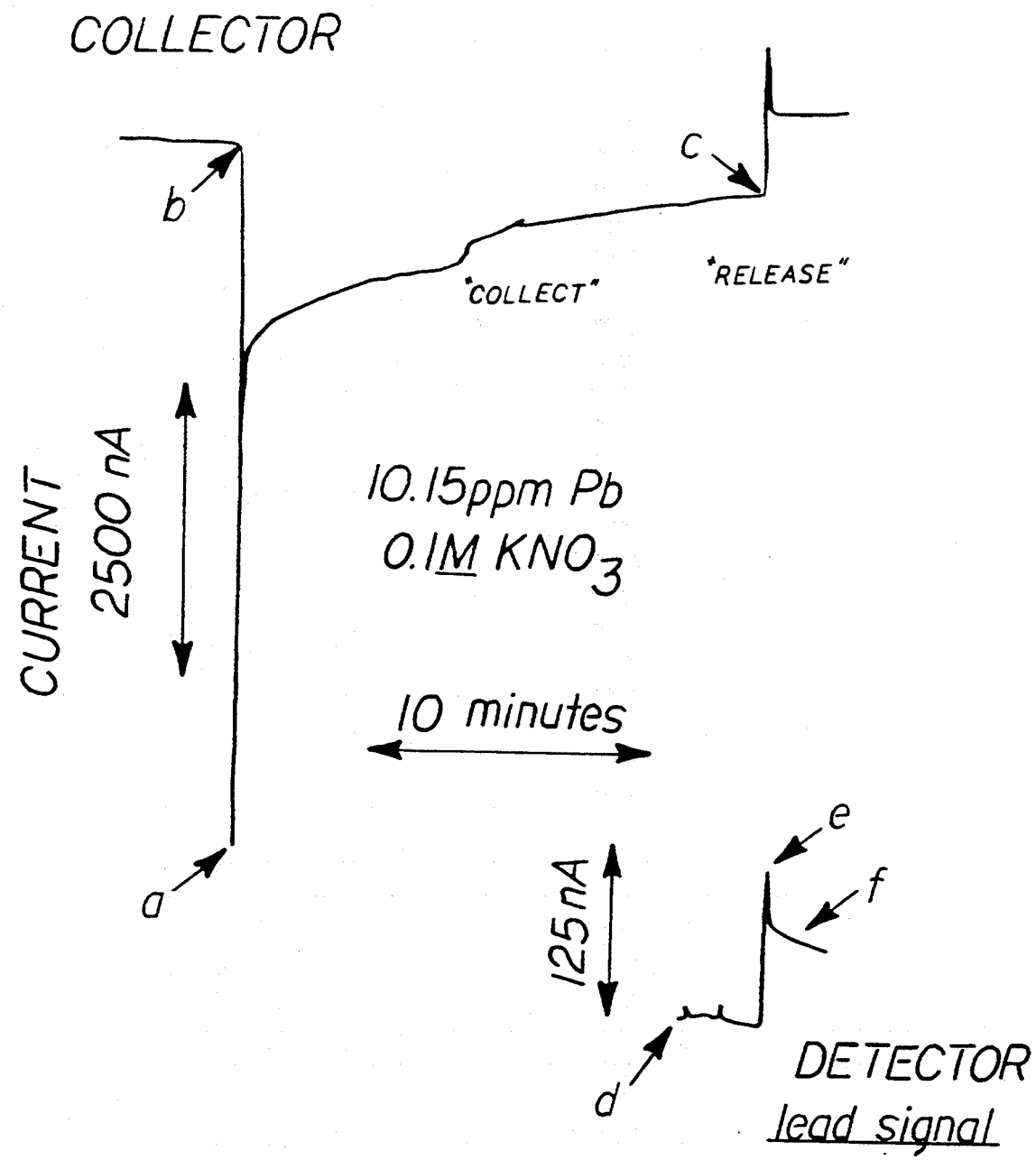
FIG. 4 is a graph showing the effect on the collector electrode and detector electrode in a sample solution containing 10 ppm of lead when subjected to a voltage sequence in accordance with the invention.
Figure 5:
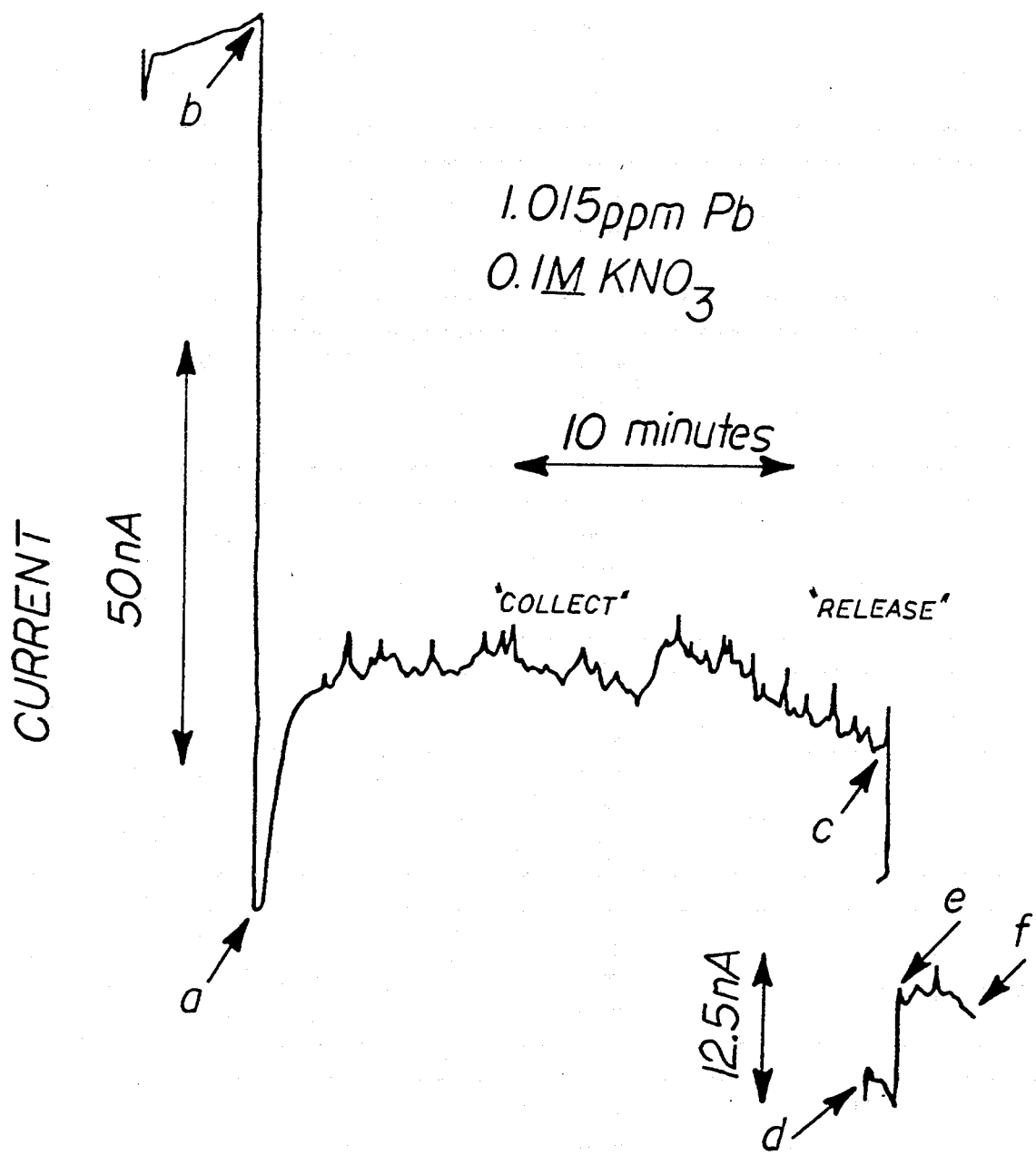
FIG. 5 is a graph showing the effect on the collector electrode and detector electrode in a sample solution containing 1.0 ppm of lead when subjected to a voltage sequence in accordance with the invention.
Figure 6:
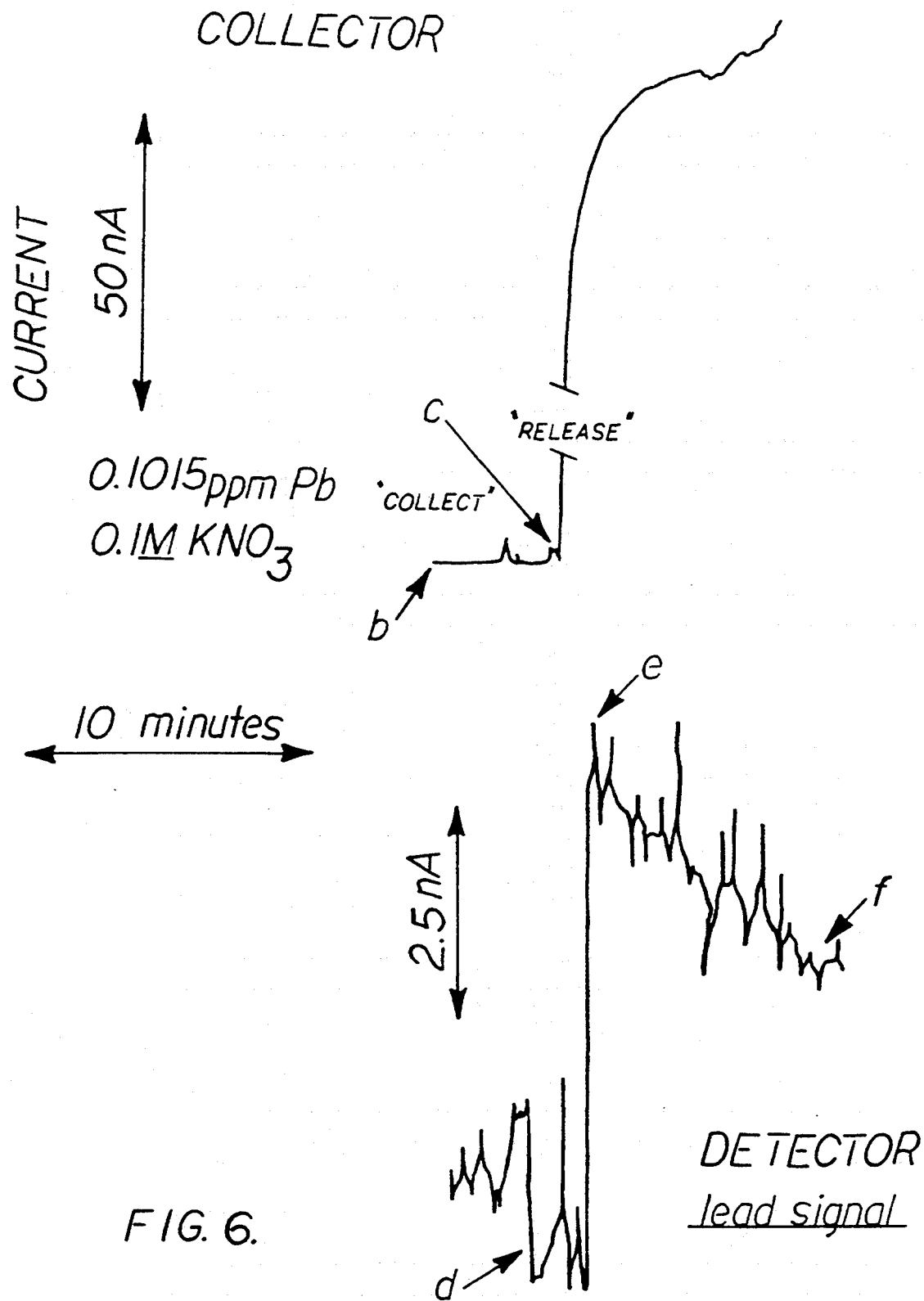
FIG. 6 is a graph showing the effect on the collector electrode and detector electrode in a sample solution containing 0.102 ppm of lead when subjected to a voltage sequence in accordance with the invention.

A series of experiments tested the reproducibility and linearity of a detector signal corresponding to the amount of lead in a solution introduced in a static cell. FIGS. 4, 5, and 6 are graphs showing the result from a) 10.15 parts per million (ppm) of Pb in 0.1 $MKNO_3$; b) 1.012 ppm of Pb in 0.1 $MKNO_3$; and c) 0.102 ppm of Pb in 0.1 $MKNO_3$ to form sample solutions. The solutions were introduced into a cell, such as chamber 22, containing a transducer having a Hg film coating thickness of 110 nm on the digits of both collector array electrodes 36 and detector array electrodes 34. A potential was placed across the collector and detector array electrodes in accordance with the sequence shown in Table II.

TABLE II

Potential Control of Collector and Detector Array Electrodes

| Time, min. | Collector, V vs. Ag/AgCl | Detector, V vs. Ag/AgCl | Comments |
|---|---|---|---|
| 0 | −0.20 | −0.20 | Clean electrode |
| 0–6 | −0.65 | −0.40 | deposit at collector |
| 6–12 | −0.65 | −0.65 | get detector ready |
| 12–18 | −0.40 | −0.65 | strip from collector |

Referring to FIGS. 4, 5, and 6 a trace of the results from the experiment are shown. First, an initial current spike to point a of the collector electrode array 36 occurs once the potential of collector electrode array 36 is changed from a cleaning potential of −0.2 V to a deposition potential −0.65 V at point b. Some of this current spike is probably caused by the reduction of dissolved oxygen which was present at around 6 parts-per-thousand (ppt). As the lead reduction continues and is concentrated from the solution into the Hg coating on the collector digits 40c, and the oxygen is being reduced, i.e., consumed, the current decreases over a first time period of about 12 minutes, then the collector potential is switched to −0.4 V for a second time period of about 6 minutes. The detector electrode array 34 initially has its potential changed from −0.2 V to −0.4 V during a third period of time corresponding to the first half, i.e., about the first six minutes of the first time period so that the detector electrode array 34 is in a ready state (not shown). Then, for a fourth time period corresponding to when the collector electrode array is set at −0.65 V for the last 6 minutes of the first time period, the detector electrode 34 is set to a potential of −0.65 V. Next, collector electrode array 36 has its potential switched to −0.4 V at point c for the second period of time enabling the accumulated lead to be released or stripped from the mercury coated, collector electrode array 36. Concurrently with the release of the lead from collector electrode array 36, the potential of detector electrode array 34 is at −0.65 V, at point d. A clear peak at point e and a current plateau along section f form as the concentrated wave of released lead diffuses across detector electrode array 34.

Figure 7:
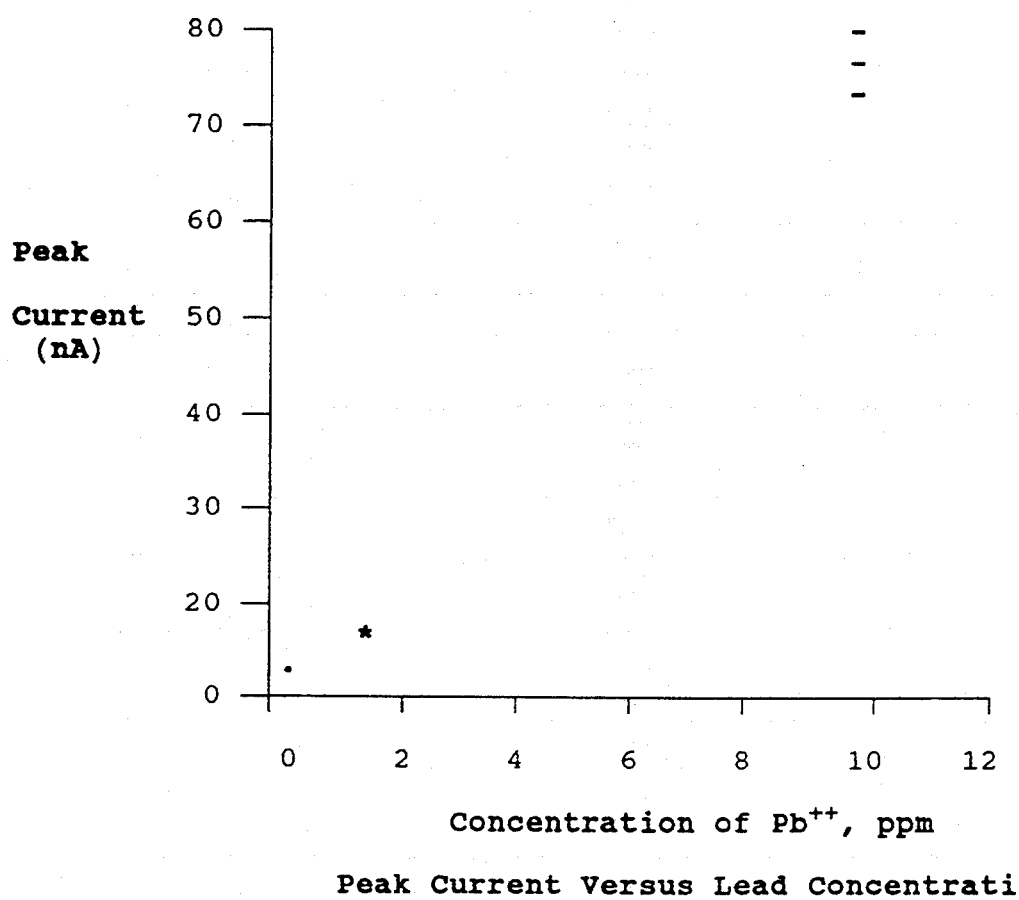
FIG. 7 is a chart showing a plot of P current vs. concentration of lead ions for three tests.

Referring to FIG. 7, there is shown a plot of peak current (the reading from detector electrode 34) versus concentration of lead ions for three separate tests of three different concentrations of lead, i.e., 10 ppm, 1 ppm and 0.1 ppm, in 0.1 MKNO$_3$. The peak current is proportional to the amount of lead in the solution. The repeatability of the three experiments for each of the lead concentrations is indicated by Chart I, where the relative standard deviation ranges from about 6.1 to about 6.7%. Note that at 0.1 ppm and at 1 ppm, the results from three tests are so close that they are indicated by a single point and single asterisk.

The experimental results discussed above support the principle of single-potential control of a transducer 24 disposed in a quiescent solution which contain trace amounts of lead. The transducer can remove the dissolved oxygen in situ via electrochemical reduction to a level adequate for lead analysis. These results indicate that the device is easily capable of discerning lead in paint around the level of about 0.1 to about 10 mg/cm$^2$. Typically less than about 10 mL of solvent will be used for a paint sample having a size of approximately 0.5 cm$^2$ to about 1.0 cm$^2$. This results in approximately 5 ppm to about 50 ppm lead in the solution and may also be suitable for water or blood analysis.

TABLE III

Potential Control of Collector and Detector Array Electrodes Modified for Excess Cadmium and Copper

| Time, min. | Collector, V vs. Ag/AgCl | Detector, V vs. Ag/AgCl | Comments |
|---|---|---|---|
| 0 | −0.20 | −0.20 | Clean electrode |
| 0–6 | −0.40 | off | deposit at collector |
| 6–12 | −0.40 | −0.30 | get detector ready |
| 12–18 | −0.25 | −0.30 | strip from collector |

Cadmium, copper, and tin are thought to be a source of potential interference with the measurement of lead, this is due to either their close stripping potential compared to lead in the case of Cd and Sn, or because of their expected presence in solutions derived from paint. Single potential control, as shown in Table III, coupled with collector and detector electrode arrays 36 and 34 can discriminate for lead. Lead selectivity is provided by reducing the lead ions and depositing them on the collector electrode array 36 at potentials negative enough to reduce and collect the lead but not negative enough to reduce cadmium. Copper will be collected at these potentials as well. However, by stripping the lead at a potential negative of the copper stripping potential, no accumulated copper is released or stripped as copper ion, and thus is not detected at the detector electrode array 34.

Another series of three tests for each of different solutions containing lead, cadmium and copper was conducted with the potential sequences set in accordance with Table II. In the absence of cadmium and copper, the potential as set in accordance with Table II. However, as the concentration of copper and cadmium increased, the potentials were adjusted so that in the case of a ten-fold excess of cadmium and copper over lead, the potentials were adjusted away from the cadmium deposition and detection potentials as shown in Table III.

TABLE IV

Lead Signals in a Matrix of Cadmium and Copper

| Solution, ppm | | | Peak Current | |
|---|---|---|---|---|
| Pb | Cd | Cu | nA | Average, std, rsd |
| 10 | 0 | 0 | 27.5, 35.0, 33.5 | 32.0 ± 3.2 (10*) |
| 10 | 1 | 1 | 35.0, 36.0, 34.5 | 35.2 ± 0.62 (1.8%) |
| 10 | 100 | 100 | 40.5, 34.0, 25.0 | 33.2 ± 6.4 (19%) |

Table IV summarizes the peak current output signal from detector electrode array 34 from these experiments. Instead of collecting both cadmium and lead, only lead was deposited. The results listed in Table IV demonstrate that with proper selection of collection and detection electrode potentials, lead can be detected in a matrix of copper and cadmium.

A solution containing the nitrate anion will place the stripping potential for Sn very close to that of lead. By adding a small quantity, i.e., between about 1.0 mM and about 50 mM and preferably about 25 mM of fluoride (F$^-$), the potential of the tin can be shifted to a more negative value and thus no current for tin will be detected when using the potentials selector for lead. By shifting the potential of the tin, the potential regime of Table III can be used to measure lead in a sample containing copper, cadmium, or tin.

A suitable mixed organic system, such as a solvent system for extracting Pb from paint can be 0.1N HNO$_3$ with methylene chloride and methyl ethyl ketone mixed in a 50:50 volumetric ratio. This system was experimentally shown to enable the extraction of lead after dissolving the paint's organic phase. In another test, a paint sample was subjected to only an acid solution. The solids were filtered before analysis. The extraction solvent could be further modified by the inclusion of a complexing agent such as EDTA or NTA.

While the present invention has primarily been explained with respect to determining the concentration of lead, it is also within the terms of the invention to determine the amounts of other trace metals including lead, cadmium, arsenic, cobalt, chromium, iron, mercury, manganese, molybdenum, nickel, selenium, thallium, vanadium, copper, zinc, and/or tin.

While the present invention has primarily related to a method and device for detecting trace metals, it could also determine the concentration of all compounds typically analyzed by polarography or hanging mercury drop electrodes. For example, some neutral electro-active compounds and charged electro-active ions capable of detection could be selected from but not limited to the following:

CYANIDES
SULFITES
HALIDES (i.e., Cl—, Br—, I—) HALIDE or SULFUR containing DRUGS, Pesticides, or COMPOUNDS (for example, penicillins, tetracyclines, parathions, thioacids, 2-thiobarbituric acid, ethylestradiol, methyl testosterone, chloramphenicol, 1-2 dibromoethane, methylenebisthiocyanate, thiourea)
OXYANIONS (for example, $[MOO_4]^{2-}$, $[CRO_4]^{2-}$, $[WO_4]^{2-}$, $[VO_3]^{2-}$)
PHOSPHATES
SULFIDES
FLAVINS (for example riboflavin )
PURINE derivatives
PYRIMIDINE derivatives common bases of NUCLEIC ACIDS (adenine, guanine, cytosine, uracil, and thymine)
COENZYMES (for example NADH
ORGANIC Acids (for example, ascorbic acid, maleic acid, fumaric acid)
ALDEHYDES (such as formaldehyde)
QUINONES (such as anthraquinone)
PHENOLS (such as p-methoxyphenol)
CATECHOLS (for example, $\tau$-butylcatecol, resorcinol)
PHARMACEUTICALS (such as, quinine, oxyphenbutazone, phenylbutazone, aldosterone)
HYDRAZINE and hydrazine derivatives
NITRATES AND NITRITES
THIOSULFATES It is apparent that there has been provided in accordance with this invention apparatus and methods for quickly and easily detecting trace amounts of electro-active substances, such trace metals that satisfy the objects, means and advantages set forth hereinbefore. According to the invention a transducer comprising interdigitated electrode arrays can be modified by coating the digits with mercury. Then, a small sample of paint digested in an organic solution with acid is placed in a portable, hand-held detector system and trace amounts of lead or other metals can be determined with a single potential control.

While the invention has been described in combination with embodiments thereof, it is evident that many alternatives, modifications, and variations will be apparent to those skilled in the art in light of the foregoing teachings. Accordingly, the invention is intended to embrace all such alternatives, modifications and variations as fall within the spirit and scope of the appended claims.

We claim:

1. A method of trace substance analysis, comprising the steps of:
   introducing a solution having a low concentration of at least one metallic or non-metallic, electro-active substance into a chamber containing a transducer having a collector electrode array interdigitated with a detector electrode array;
   applying a first reducing potential to said collector electrode array for a first period of time whereby ions of said at least one metallic or non-metallic, electro-active substance are reduced from said solution and concentrated on said collector electrode array;
   applying a first oxidizing potential to said collector electrode array for a second period of time and simultaneously applying a detecting potential to said detector electrode array for said second period of time whereby said at least one metallic or non-metallic, electro-active substance concentrated on said collector array is stripped as ions from said collector electrode array back into said solution; and
   measuring a current across said detector electrode array during said second period of time to determine the amount of said at least one metallic or non-metallic, electro-active substance within said solution.

2. The method of claim 1 including the step of interposing spaced digits of a monolithic, digitated array forming said collector electrode array between spaced digits of a monolithic, digitated array forming said detector electrode array so that adjacent digits are spaced a distance of about 5 $\mu$m to about 15 $\mu$m.

3. The method of claim 2 including the step of coating one or more of said digits of both said collector electrode array and said detector electrode array with a layer of mercury.

4. The method of claim 2 including the step of constructing said spaced digits of said collector electrode array and said detector electrode array from a material selected from the group consisting of gold, platinum, iridium, indium, tin oxide, indium on tin oxide, Ebonex TM, silver graphite glassy carbon, and conductive carbon.

5. The method of claim 1 including the step of selecting said at least one metallic or non-metallic electro-active substance from a neutral or charged species consisting essentially of carbon, nitrogen, oxygen, sulfur, phosphorous, halides, trace metals, or a combination thereof.

6. The method of claim 5 including the step of selecting said at least one metallic or non-metallic, electro-active species from compounds consisting of sulfites or cyanides.

7. The method of claim 5 including the step of selecting said at least one metallic or non-metallic, electro-active species from compounds consisting ionic or neutral organic compounds.

8. The method of claim 1 including the step of selecting said at least one electro-active substance from a low concentration of at least one trace metal.

9. The method of claim 8 including the step of selecting said at least one trace metal from the group consisting of lead, cadmium, silver, copper, zinc, arsenic, cobalt, chromium, iron, manganese, mercury, molybdenum, nickel, selenium, thallium, vanadium, and tin.

10. The method of claim 9 including the step of selecting said at least one trace metal as lead.

11. The method of claim 7 including the steps of:
applying said first reducing potential of about −0.4 to about −1.2 volts versus Ag/AgCl reference to said collector array for said first period of time;
applying said first oxidizing potential of about 0.10 to about −0.35 volts versus Ag/AgCl reference to said collector electrode array for said second period of time; and
applying said detecting potential of about −0.40 to about −0.70 volts versus Ag/AgCl reference to said detector electrode array for said second period of time.

12. The method of claim 11 including the steps of:
applying a first cleaning potential of about 0.10 to about −0.20 volts versus Ag/AgCl reference to said collector electrode array for a third period of time of about 0.5 to about 20 minutes to clean said collector electrode array; and
applying a second cleaning potential of about 0.10 to about −0.20 volts versus Ag/AgCl reference to said detector electrode array for said third period of time to clean said detector electrode array.

13. The method of claim 12 including the steps of:
selecting said first period of time between about 0.5 and about 20 minutes;
selecting said second period of time between about 0.5 and about 20 minutes; and
selecting said third period of time between about 0.5 and about 20 minutes.

14. A method of trace substance analysis, comprising the steps of:
introducing a solution having a low concentration of at least one electro-active substance into a chamber containing a transducer having a collector electrode array interdigitated with a detector electrode array;
applying a first oxidizing potential to said collector electrode array for a first period of time whereby ions of said at least one electro-active substance are oxidized from said solution and concentrated on said collector electrode array;
applying a first reducing potential to said collector electrode array for a second period of time and simultaneously applying a detecting potential to said detector electrode array for said second period of time whereby said at least one electro-active substance concentrated on said collector electrode array is stripped from said collector electrode array back into said solution; and
measuring the current across said detector electrode array during second period of time to determine the amount of said at least one electro-active substance within said solution.

15. A method of claim 14 including the step of selecting said electro-active substance from at least one metallic or non-metallic substance selected from the group of neutral or charged species consisting essentially of carbon, nitrogen, oxygen, sulfur, phosphorous, halides, the metals, or a combination thereof.

16. A system for trace substance analysis, comprising:
means for introducing a solution having a low concentration of at least one electro-active substance into a chamber containing a transducer having a collector electrode array interdigitated with a detector electrode array;
means for applying a first reducing potential to said collector electrode array for a first period of time whereby ions of said at least one electro-active substance are reduced from said solution and concentrated on said collector electrode array;
means for applying a first oxidizing potential to said collector electrode array for a second period of time;
means for applying a detecting potential to said detector electrode array during said second period of time whereby said at least one electro-active substance on said collector electrode array is stripped from said collector electrode array back into said solution; and
means for measuring current across said detector electrode array during said second period of time to determine the amount of said at least one electro-active substance within said solution.

17. The system of claim 16 wherein said collector electrode array and said detector electrode array are each constructed of a monolithic, digitated array having a plurality of spaced digits.

18. The system of claim 17 wherein at least one of said plurality of spaced digits is coated with a layer of mercury.

19. The system of claim 18 wherein said spaced digits of said collector electrode array and said detector electrode array are constructed from a material selected from the group consisting of gold, platinum, iridium, indium tin oxide, indium and tin oxide Ebonex TM, silver, graphite, glassy carbon, and conductive carbon.

20. The system of claim 19 wherein said at least one electro-active substance is a neutral or charged species consisting essentially of carbon, nitrogen, oxygen, sulfur, phosphorous, halides, trace metals, or a combination thereof.

21. The system of claim 20 wherein said at least one electro-active substance is a low concentration of at least one trace metal.

22. The system of claim 21 wherein said at least one trace metal is from the group consisting of lead, cadmium, silver, copper, zinc, arsenic, cobalt, chromium, iron, manganese, mercury, molybdenum, nickel, selenium, thallium, vanadium, and tin.

23. The system of claim 20 wherein said at least one trace metal is lead.

24. A system for trace substance analysis, comprising:
means for introducing a solution having a low concentration of at least one electro-active substance into a chamber containing a transducer formed of a collector electrode array interdigitated with a detector electrode array;
means for applying a first oxidizing potential to said collector electrode array for a first period of time whereby said species of said at least one electro-active substance are oxidized from said solution and concentrated on said collector electrode array;
means for applying a first reducing potential to said collector electrode array for a second period of time;
means for applying a detecting potential to said detector electrode array during said second period of time whereby said at least one electro-active substance concentrated on said collector array is stripped from said collector electrode array back into said solution; and means for measuring current across said detector electrode array during said second period of time to determine the amount of said at least one electro-active substance within said solution.

25. The system of claim 24 including means for selecting said electro-active species from at least one metallic or non-metallic, neutral or charged species consisting essentially of carbon, nitrogen, oxygen, sulfur, phosphorous, halides, the metals, or a combination thereof.

26. The system of claim 25 including:
means for applying said first reducing potential of about $-0.4$ to about $-1.2$ volts versus Ag/AgCl reference to said collector electrode array for said first period of time;
means for applying said first oxidizing potential of about $0.10$ to about $-0.35$ volts versus Ag/AgCl reference to said collector electrode array for said second period of time; and
means for applying said detection potential of about $-0.40$ to about $-0.70$ volts versus Ag/AgCl reference to said detector electrode array for said second period of time.

27. The system of claim 25 including:
means for applying a first cleaning potential of about $0.10$ to about $-0.20$ volts versus Ag/AgCl reference to said collector electrode array for a third period of time of about 0.5 to about 20 minutes to clean said collector electrode array; and
means for applying a second cleaning potential of about $0.10$ to about $-0.20$ volts versus Ag/AgCl reference to said detector electrode array for said third period of time to clean said detector electrode array.

28. An interdigitated array constructed of a first electrode array and a second electrode array, each of said first and second electrode arrays being constructed of a monolithic, digitated array having a plurality of spaced digits each coated with a layer of mercury, said spaced digits are constructed of a material selected from the group consisting of gold, platinum, iridium, indium, tin oxide, indium and tin oxide, Ebonex TM, silver graphite glass, carbon, and conductive carbon.

29. The interdigitated array of claim 28 wherein said layer of mercury is less than about 1000 nm thick.

30. The interdigitated array of claim 29 wherein said layer of mercury is preferably from about 100 nm to about 500 nm thick.

31. The interdigitated array of claim 28 wherein each of said monolithic, digitated arrays has four electrodes, and two of said electrodes on said monolithic, digitated array are reference and auxiliary electrodes.

* * * * *